United States Patent
Eberli et al.

(10) Patent No.: US 12,370,221 B2
(45) Date of Patent: Jul. 29, 2025

(54) METHOD FOR XENO-FREE GENERATION OF A POPULATION OF hMPC

(71) Applicant: UNIVERSITÄT ZÜRICH, Zurich (CH)

(72) Inventors: Daniel Eberli, Zürich (CH); Deana Mohr, Kreuzlingen (CH); Souzan Salemi, Zürich (CH); Fahd Azzabi Zouraq, Lausanne (CH)

(73) Assignee: UNIVERSITÄT ZÜRICH, Zurich (CH)

( * ) Notice: Subject to any disclaimer, the term of this patent is extended or adjusted under 35 U.S.C. 154(b) by 719 days.

(21) Appl. No.: 17/049,397

(22) PCT Filed: May 6, 2019

(86) PCT No.: PCT/EP2019/061561
§ 371 (c)(1),
(2) Date: Oct. 21, 2020

(87) PCT Pub. No.: WO2019/215090
PCT Pub. Date: Nov. 14, 2019

(65) Prior Publication Data
US 2021/0244770 A1 Aug. 12, 2021

(30) Foreign Application Priority Data
May 8, 2018 (EP) ..................................... 18171162

(51) Int. Cl.
| | |
|---|---|
| A61K 35/34 | (2015.01) |
| A61K 38/01 | (2006.01) |
| C12N 5/00 | (2006.01) |
| C12N 5/077 | (2010.01) |
| A61P 13/00 | (2006.01) |
| A61P 13/10 | (2006.01) |

(52) U.S. Cl.
CPC ............ *A61K 35/34* (2013.01); *A61K 38/014* (2013.01); *C12N 5/0031* (2013.01); *C12N 5/0658* (2013.01); *C12N 2500/36* (2013.01); *C12N 2501/11* (2013.01); *C12N 2501/115* (2013.01); *C12N 2501/135* (2013.01); *C12N 2501/33* (2013.01); *C12N 2533/54* (2013.01)

(58) Field of Classification Search
CPC .... A61K 35/34; A61K 38/014; C12N 5/0658; C12N 2533/54
See application file for complete search history.

(56) References Cited

U.S. PATENT DOCUMENTS
| | | |
|---|---|---|
| 5,130,141 A | 7/1992 | Law et al. |
| 2014/0227233 A1 | 8/2014 | Firouz |

FOREIGN PATENT DOCUMENTS
| | | |
|---|---|---|
| WO | 2008/086040 A1 | 7/2008 |
| WO | 2016/138289 A1 | 9/2016 |

OTHER PUBLICATIONS

Eberli et al., (2012), Muscle precursor cells for the restoration of irreversibly damaged sphincter function. Cell Transplantation, 21(9), 2089-2098 (Year: 2012).*
Eberli et al., (2009) Optimization of human skeletal muscle precursor cell culture and myofiber formation in vitro, Methods, 47(2), 98-103 (Year: 2009).*
Haralampieva et al., (2016) Noninvasive PET imaging and tracking of engineered human muscle precursor cells for skeletal muscle tissue engineering. The Journal of Nuclear Medicine, 57(9), 1467-1473 (Year: 2016).*
Stölting et al., (2012), In vivo electromagnetic stimulation supports muscle regeneration after stem cell injection by boosting muscular metabolism and stimulationg nerve ingrowth. Journal of Urology, 187(4S), e85-e86 (Year: 2012).*
Zouraq et al., (2012) Xeno-free culturing of human muscle precursor cells (MPC) for clinical application. in 3rd Termis World Congress, Tissue Engineering and Regenerative Medicine, Vienna (Year: 2012).*
Saury et al., (2018) Human serum and platelet lysate are appropriate xeno-free alternatives for clinical-grade production of human MuStem cell batches. Stem Cell Research & Therapy, 9, 128 (Year: 2018).*
International Preliminary Report on Patentability dated Nov. 10, 2020 in International Application No. PCT/EP2019/061561.
Pentti J. Kiilholma et al., "Complications of Teflon Injection for Stress Urinary Incontinence", Neurourology and Urodynamics, 1993, vol. 12, pp. 131-137 (7 pages total).
Andrea Barbero et al., "Growth Factor Supplemented Matrigel Improves Ectopic Skeletal Muscle Formation—A Cell Therapy Approach", Journal of Cellular Physiology, 2001, vol. 186, No. 2, pp. 183-192 (10 pages total).
D.D. Chandi et al., "Functional extracorporeal magnetic stimulation as a treatment for female urinary incontinence: 'the chair'", BJU International, 2004, vol. 93, No. 4, pp. 539-542 (5 pages total).
Silvia Castegnaro et al., "Effect of Platelet Lysate on the Functional and Molecular Characteristics of Mesenchymal Stem Cells Isolated from Adipose Tissue", Current Stem Cell Research & Therapy, 2011, vol. 6, No. 2, pp. 105-114 (10 pages total).
Charlotte Saury et al., "Human serum and platelet lysate are appropriate xeno-free alternatives for clinical-grade production of human MuStem cell batches", Stem Cell Research & Therapy, 2018, vol. 9, No. 128, pp. 1-20 (20 pages total).
Fahd Azzabi et al., "Culturing Human Muscle Precursor Cells (MPCS) with Xeno-Free Medium: GMP and Clinical Application Preparation", The Journal of Urology, 2013, vol. 189, No. 4S, p. 106 (1 page total).
Samir Ranjitkar et al., "The use of pooled human platelet lysate for isolation and ex vivo expansion of skeletal myoblasts for clinical use", European Cells and Materials, 2017, vol. 33, Suppl. 2 (2 pages total).

(Continued)

*Primary Examiner* — Kara D Johnson
(74) *Attorney, Agent, or Firm* — Sughrue Mion, PLLC

(57) ABSTRACT

The present invention concerns a method of generating a population of skeletal muscle derived human muscle precursor cells. For this purpose, a specialized FBS-free cell growth medium is used. The invention further concerns a composition comprising such a population of hMPCs for use as a medicament, especially in the treatment of skeletal muscle dysfunction.

15 Claims, 8 Drawing Sheets

(56) References Cited

OTHER PUBLICATIONS

Brian C. Syverud et al., "Isolation and Purification of Satellite Cells for Skeletal Muscle Tissue Engineering", J Regen Med., 2014, vol. 3, No. 2, pp. 1-20 (20 pages total).
R. Ian Freshney, "Culture of Animal Cells: A Manual of Basic Technique and Specialized Applications, Sixth Edition", 2010, pp. 211 & 411 (2 pages total).
Hang Yin et al., "Satellite Cells and the Muscle Stem Cell Niche", Physiol Rev, 2013, vol. 93, pp. 23-67 (45 pages total).
Thomas A. Rando et al., "Methods for Myoblast Transplantation", Methods in Cell Biology, vol. 52, 1997, pp. 261-272 (13 pages total).
Daniel Eberli et al., "A canine model of irreversible urethral sphincter insufficiency", BJU International, 2008, 6 pages.
Von Bonin et al., "Treatment of refractory acute GVHD with third-party MSC expanded in platelet lysate-containing medium", Bone Marrow Transplantation, 2009, 8 pages.
Daniel Eberli et al., "Muscle Precursor Cells for the Restoration of Irreversibly Damaged Sphincter Function", Cell Transplantation, vol. 21. 2012, 10 pages.
David K. Kramer et al., "Effect of serum replacement with Plysate on cell growth and metabolism in primary cultures of human skeletal muscle", Cytotechnology 2005, 8 pages.
Daniel Eberli et al., "Optimization of human skeletal muscle precursor cell culture and myofiber formation in vitro", Methods 47, 2009, 6 pages.
Yan Wei et al., Human skeletal muscle-derived stem cells retain stem cell properties after expansion in myosphere culture, ScienDirect, 2011, 12 pages.
Karen Bieback, "Platelet Lysate as Replacement for Fetal Bovine Serum in Mesenchymal Stromal Cell Cultures", Transfusion Medicine and Hemotherapy, 2013, 10 pages.
Jae Heon Kim et al., "Stem Cell Therapy in Bladder Dysfunction: Where Are We? And Where Do We Have to Go?", BioMed Research International, 2013, 10 pages.
Katharina Schallmoser et al., "Human platelet lysate can replace fetal bovine serum for clinical-scale expansion of functional mesenchymal stromal cells", Transplantation and Cellular Engineering, 2007, 12 pages.
Ren'e Yiou et al., "Restoration of Functional Motor Units in a Rat Model of Sphincter Injury by Muscle Precursor Cell Autografts", Transplantation, 2003, 8 pages.
Teruhiko Yokoyama et al., "Autologous Primary Muscle-Derived Cells Transfer into the Lower Urinary Tract", Tissue Engineering, 2001, 10 pages.
International search report for PCT/EP2019/061561 dated Jun. 13, 2019.
Written opinion for PCT/EP2019/061561 dated Jun. 13, 2019.
Fan Yingchang, Heart Disease and Cell Transplantation, Tianjin: Tianjin Science and Technology Press, paragraph 4 on p. 119, Apr. 2008, pp. 118-129 (12 pages).
Barnacal et al., Medical treatment in Western Countries, 1998, Pulsed Electromagnetic Stimulation Therapy, China Council for the Promotion of International Trade; China Chamber of International Commerce, pp. 28-29 (3 pages).
Partial English Translation of Communication dated Jun. 3, 2023, issued in Chinese Application No. 201980030514.2.
J. Koudy Williams, et al., "The Dose-Effect Safety Profile of Skeletal Muscle Precursor Cell Therapy in a Dog Model of Intrinsic Urinary Sphincter Deficiency", Stem Cells Translational Medicine, 2015, vol. 4, pp. 286-294.
Fahd Azzabi Zouraq, et al., "Skeletal Muscle Regeneration for Clinical Application", Regenerative Medicine and Tissue Engineering, 2013 (34 pages) Accessed via the Internet: http://dx.doi.org/10.5772/55739.
Deana Haralampieva, et al., "Human Muscle Precursor Cells Overexpressing PGC-1α Enhance Early Skeletal Muscle Tissue Formation", Cell Transplantation, 2017, vol. 26, pp. 1103-1114.
Eduardo Fernandez-Rebollo, et al., "Human Platelet Lysate versus Fetal Calf Serum: These Supplements Do Not Select for Different Mesenchymal Stromal Cells", Scientific Reports, vol. 7, No. 5132, Jul. 11, 2017, pp. 1-8.
Mariluz P. Mojica-Henshaw, et al., "Serum-converted platelet lysate can substitute for fetal bovine serum in human mesenchymal stromal cell cultures", Cytotherapy, 2013, vol. 15, pp. 1458-1468.
Haralampieva et al., "MP12-19 Non-Invasive Tracking of Muscle Precursor Cells for Sphincter Muscle Engineering", The Journal of Urology, 2014, p. e113 (1 page).
"Cook Medical Introduces Stemulate™ Human Platelet Lysate Cell Culture Media Supplement", International Society for Cellular Therapy Meeting, Apr. 23-26, 2014 (1 page).
Guang-Zhen Jin, et al.; Effects of Type I Collagen Concentration in Hydrogel on the Growth and Phenotypic Expression of Rat Chondrocytes; The Korean Tissue Engineering and Regenerative Medicine Society and Springer Science+Business Media Dordrecht; Published Jun. 30, 2017; pp. 383-391.
Jennifer Kim MD, et al.; Muscle Tissue Engineering for Partial Glossectomy Defects; American Medical Association, ARCH Facial Plastic Surgery; www.archfacial.com; Published Sep. 2003; pp. 403-407.
Taimoor H. Qazi, et al.; Biomaterial Based Strategies for Skeletal Muscle Tissue Engineering: Existing Technologies and Future Trends; Biomaterials Journal 53; www.elsevier.com/locate/biomaterials; Published Feb. 24, 2015; pp. 502-521.
Kenneth M. Peters, et al.; Autologous Muscle Derived Cells for Treatment of Stress Urinary Incontinence in Women; The Journal of Urology; www.jurology.com; vol. 192; Published Aug. 2014; pp. 1-8.
Dawn M. Delo, et al.; Angiogenic Gene Modification of Skeletal Muscle Cells to Compensate for Ageing-Induced Decline in Bioengineered Functional Muscle Tissue; Wake Forest Institute for Regenerative Medicine, Wake Forest University Health Sciences; BJUI International; vol. 102; published Feb. 2008; pp. 878-884.
Christopher J. Centeno, et al., "Safety and Complications Reporting Update on the Re-Implantation of Culture-Expanded Mesenchymal Stem Cells Using Autologous Platelet Lysate Technique", Current Stem Cell Research & Therapy, 2011, vol. 6, pp. 368-378 (12 pages total).
Johansson et al., "Platelet lysate: a replacement for fetal bovine serum in animal cell culture?", Cytotechnology, vol. 42, 2003, pp. 67-74.

* cited by examiner

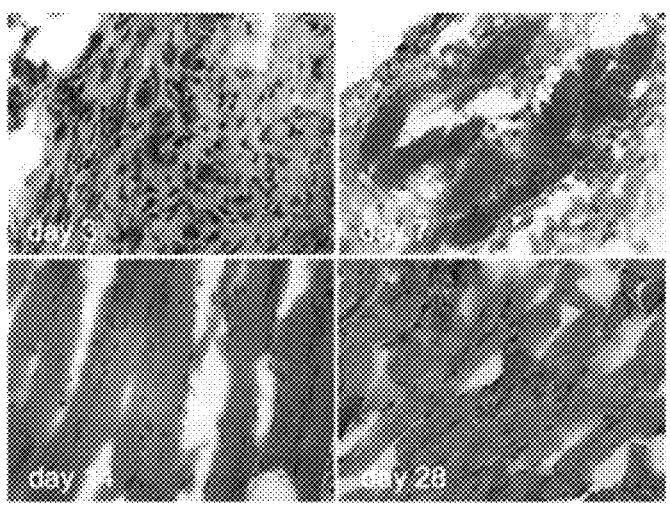
FIG. 10
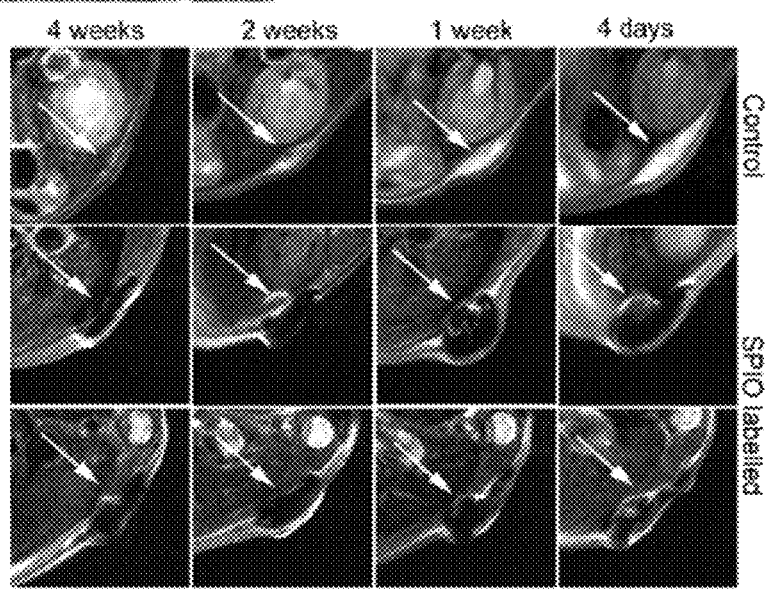
FIG. 11
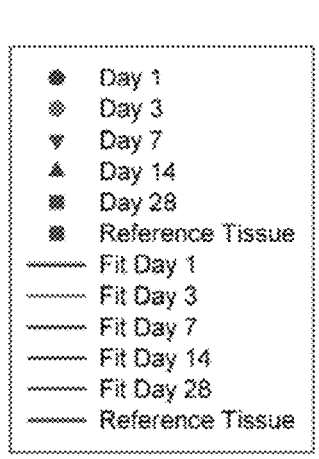
FIG. 12
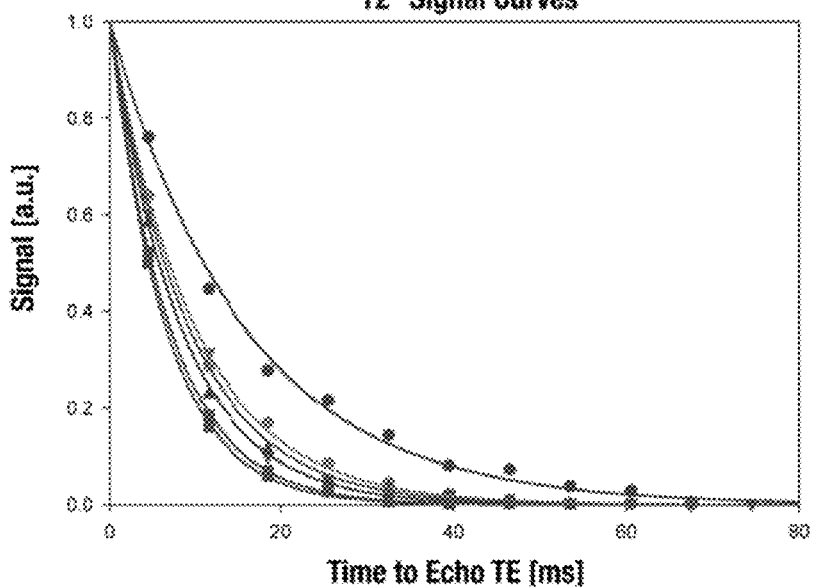

METHOD FOR XENO-FREE GENERATION OF A POPULATION OF hMPC

CROSS-REFERENCE TO RELATED APPLICATIONS

This application is a National Stage of International Application No. PCT/EP2019/061561 filed May 6, 2019, which claims priority under U.S.C. § 119 (a) to European Patent Application No. 18171162.3 filed May 8, 2018.

TECHNICAL FIELD

The present invention relates to a method for the xeno-free generation of a population of human muscle precursor cells (hMPC), a composition comprising these hMPCs, and the use of these hMPCs in the production of a composition for the treatment of skeletal muscle dysfunction, especially of stress urinary incontinence.

PRIOR ART

Urinary incontinence, the involuntary loss of urine, is a major medical issue with approximately half of the female population affected over 45 years and 17% of men over 70 years of age. Continence and micturition involve a balance between urethral closure and detrusor muscle activity. Continence is achieved by a complex interplay of urethral sphincter, bladder neck position, urethral smooth muscle, nerve integrity, vascular plexus and the surrounding tissue support.

There are different types of urinary incontinence, such as stress and urge incontinence. Stress urinary incontinence (SUI) is the loss of small amounts of urine associated with coughing, laughing, sneezing, exercising or other movements that increase intra-abdominal pressure and thus increase pressure on the bladder. The external striated urethral sphincter, which is made of skeletal muscle and therefore is under voluntary control of the somatic nervous system is, for the most part, responsible for preventing SUI. Damage to the external urethral sphincter occurs mainly during childbirth, surgical treatments or as an effect of aging. SUI is a disease affecting over 200 million people worldwide and is twice as common in women as in men, decreasing the quality of life of patients due to limited daily activities, unpleasant sensation, odor and infections caused by wet diapers. The incurring healthcare costs are significant.

Current treatment options of SUI include mainly non-surgical therapy (bladder training, dietary modifications), drug therapy and surgical therapy. These therapies offer only short-term relief and their overall success is often limited by complications (invasiveness of surgery, damage to surrounding tissues, leading to increased urinary infection rates) or side-effects (drugs, tissue damage by non-degradable biomaterials, etc.). Advances in cell therapy approaches to treat urinary incontinence show promising results towards correcting the underlying etiology using the patient's own cells. Recent advances in cell-based therapies have provided a variety of solutions to restore damaged sphincter function in patients with SUI.

U.S. Pat. No. 5,130,141 discloses the use of myoblasts for the treatment of muscle weakness in mice. A more advanced approach to muscle regeneration is by incorporating myoblasts, with or without the exogenous growth factors into three-dimensional gels of reconstituted basement membrane (Barbero et al., Growth factor supplemented matrigel improves ectopic skeletal muscle formation—a cell therapy approach, J Cell Physiol. 2001 February; 186 (2): 183-92). In these protocols, a commercially available gelatinous protein mixture secreted by murine sarcoma cells (Matrigel®) was used, which contains a high concentration of various growth factors to promote proliferation and differentiation of myoblasts.

US 2014/0227233 A1 discloses a method for the treatment of SUI by the injection of a "regenerative glue" comprising a combination of commercially available material (including biocompatible glues, fibrin glue (of human fibrinogen and human thrombin) or biocompatible gels) with mesenchymal stem cells from bone marrow or adipose tissue.

This glue was injected at the site of a damaged, absent or injured pubo-urethral ligament for replacement purposes.

WO 2016/138289 A1 discloses the potential use of smooth muscle precursor cells for the treatment of smooth muscle dysfunction.

The use of injectable bulking agents such as Teflon, bovine collagen, silicone particles and carbon beads has yielded short-term success. However, it has been reported that these bulking agents can cause chronic inflammation, foreign body giant cell response, periurethral abscess, erosion of the urethra, obstruction of the lower urinary tract with resultant urinary retention, and migration to inner organs and pulmonary embolism (Kiilholma P. et al., Complications of Teflon injections for stress urinary incontinence, Neurourol. Urodyn 12:131-137 (1993)).

The transplantation of MPCs has been investigated as a treatment for genetic and acquired muscle disorders. MPCs, in their quiescent, inactive stage as satellite cells, reside underneath the basal lamina surrounding the muscle fibers. These cells become activated upon trauma or damage and participate in tissue regeneration by migrating towards the injured area, proliferating, and fusing with each other to form myotubes, which finally mature into myofibers. The majority of MPCs are committed to the myogenic cell lineage and are therefore most suitable for skeletal muscle bioengineering. MPCs have great growth potential and are easily expanded in culture. After myotube formation, these cells become post-mitotic and begin to differentiate into mature fibers, inhibiting uncontrolled tissue growth in vivo. The potential use of injectable cultured MPCs for the treatment of SUI has been investigated in rodent and canine models and has the potential to become the first treatment to restore sphincter muscle function (Yokohama et al., Autologous Primary Muscle-Derived Cells Transfer into the Lower Urinary Tract; Tissue Engineering, 2001, 7 (4), p. 395-404; Yiou et al., Restoration of Functional Motor Units in a Rat Model of Sphincter Injury by Muscle Precursor Cell Autografts, Transplantation, 2003, 76 (7): p. 1053-60; Eberli et al., A canine model of irreversible urethral sphincter insufficiency. BJU Int, 2009, 103 (2): p. 248-53). However, these animal models do not sufficiently reflect the conditions seen in human patients.

Muscle-derived stem cells and autologous myoblast injections have been the most investigated options in humans so far. However, despite several attempts in the past, regenerative therapies of the urethral sphincter have not yet reached the clinic and are not yet part of the daily urologic practice.

Due to concerns over fetal bovine serum (FBS), its replacement is required to facilitate the transfer of this therapy into a clinical setting. So far, FBS was the standard medium supplement and source of growth factors for cell culture and tissue engineering. The use of FBS during in vitro culture expansion of progenitor cells might pose a potential hazard due to proteins and macromolecules. The internalization of these macromolecules in stem cells can transmit viral-/prion disease. Moreover, the macromolecules serve as antigenic substrates on transplanted cells and cause immunological reactions. Due to risks of xeno-immunization, transmission of pathogens, and ethical issues associated with FBS collection, suitable human alternatives for the manufacture of clinical cell therapeutic products are urgently needed. FBS is therefore not desirable due to safety and other concerns for clinical application. In some research studies, anaphylaxis and other allergic reactions have been defined in the patients transplanted with the cells supplemented with FBS.

As any drug applied in a therapeutic approach, cell products also need to meet regulatory requirements. Their production process needs to follow good manufacturing practise (GMP) in order to allow a safe application in patients. Therefore, the removal of any animal supplements from the cell culture medium represents an important step toward the clinical transfer of a muscle stem cell therapy into patients suffering from SUI, thereby avoiding adverse reactions to xenogenic proteins. This change in cell culture methodology should be implemented without affecting the main characteristics of hMPCs, i.e. their ability to form contracting muscle tissue.

Possible alternatives to FBS are media complemented with human serum, human platelet derivatives, allogenic umbilical cord blood serum or chemically defined media.

Human platelet lysate (hPL)-containing cell culture medium, or growth medium, respectively, has been described as a possible substitute for FBS-containing media for clinical-scale expansion of mesenchymal stromal cells or to expand human mesenchymal stem cells for therapeutic applications (Schallmoser et al., Human platelet lysate can replace fetal bovine serum for clinical-scale expansion of functional mesenchymal stromal cells. Transfusion 2007, 47:1436-1446; Castegnaro et al., Effect of Platelet Lysate on the Functional and Molecular Characteristics of Mesenchymal Stem Cells Isolated from Adipose Tissue. Curr Stem Cell Res Ther. 2011; 6 (2): 105-14). However, this serum change might not be tolerated by all cell types or might affect the functionality of some cultured cells. A previous study found hPL not to be a suitable replacement for FBS in culturing human skeletal muscle cells and to differentiate the cells into myotubes (Kramer et al., Effect of serum replacement with plysate on cell growth and metabolism in primary cultures of human skeletal muscle. Cytotechnology 48, 89, 2005).

Cell proliferation is medium-dependent and the mere addition of growth factors is not sufficient to sustain the expansion of cells.

It is therefore an object of the invention to provide an alternative to FBS in cell culture medium that grants the proliferation of hMPCs and enables the efficient formation of contracting tissue engineered muscles in vivo after implant. It is therefore an object of the present invention, for ethical and safety purposes, to develop a new, xeno-free (or animal-component-free) and therefore safe, GMP-compliant protocol for culture and expansion of hMPCs, i.e. for the production of a composition comprising a population of hMPCs for use in therapeutic applications, especially for the regenerative treatment of SUI in human female patients.

Finally, the present invention aims at providing an improved method of treatment for skeletal muscle dysfunction.

Neuromodulation and exercise training has been proposed as a possible treatment of deficient skeletal muscle. In humans, a magnetic coil wrapped around the quadriceps has been demonstrated to induce effortless muscle fatigue and training. A similar device for exercising the pelvic floor was designed in which magnetic pulses converged into a coil placed inside a chair seat (Chandi et al., Functional extracorporeal magnetic stimulation as a treatment for female urinary incontinence: "the chair". BJU Int, 2004. 93 (4): p. 539-42).

Neuro-muscular electromagnetic stimulation (NMES), which induces muscle twitch, has been proposed as a therapeutic modality for skeletal muscle diseases. Blaganje et al. disclosed in 2012 the successful treatment of SUI by ultrasound-guided autologous myoblast injections into the external urethral sphincter, preceded and followed by electrical stimulation. It is therefore a further object of the invention to provide an optimized method of treatment of SUI in human female patients, using cells and stimulation.

SUMMARY OF THE INVENTION

The application of human muscle precursor cells (hMPC) in tissue engineering is a promising approach for the treatment of stress urinary incontinence (SUI) by regenerating contractile muscle. For this purpose, a method for generating a composition for use as a medicament in such therapeutic applications is suggested. The composition comprises a population of skeletal muscle derived hMPCs (or muscle regenerating cells), the generation of which is also provided as an inventive method.

The invention, according to a first aspect, therefore concerns a method of generating an autologous population of human muscle precursor cells derived from skeletal muscle, the method comprising at least the following steps: First, a human tissue sample is obtained by a skeletal muscle biopsy of a human patient.

Preferably, a skeletal muscle biopsy is obtained from a human female patient, however, also skeletal muscle biopsies of male patients, e.g. to treat possible SUI after prostataectomy, may be useful. Preferably, the skeletal muscle biopsy is taken from a tissue selected from the group consisting of: musculus soleus, rectus abdominis, quadriceps femoris, vastus lateralis.

The musculus soleus (of the left or right leg) is chosen for biopsy due to its similarity in composition to the sphincter muscle and its easy accessibility. As an alternative, e.g. the vastus lateralis muscle can be used. In case transport of the biopsy is necessary after surgical removal, the biopsy can be transported in a transport medium containing an antibiotic agent and PBS.

After washing and desinfection, the muscle biopsy is surgically cleared of remains of fat- and/or tendon- and/or connective tissues, then minced and digested, preferably by a mixture containing collagenase and dispase. Preferably, a mixture of collagenase type I 0.2% (w/v) and dispase 0.4% (w/v) is used. The enzymatic reaction is terminated, preferably with a cell culture medium, i.e. growth medium containing 10% human platelet lysate (hPL), preferably 10% pooled human platelet lysate (phPL). Subsequently, individual fibres are liberated by rigorous pipetting and filtered through a strainer, preferably with a pore size of 100 μm. After centrifugation, the pellet is re-suspended in growth medium supplemented with 1% Penicillin/Streptomycin (supplemented only for this passage 0 step) and transferred into 35 mm-dishes (6-well) coated with an extracellular matrix protein, such as collagen or fibronectin, preferably collagen type I (preferably 1 mg/ml).

After digestion, after 24 h, the supernatant containing non-adhered hMPCs is re-plated into dishes coated with collagen type I, in order to reduce the number of contaminating fibroblasts, thereby yielding a population of human muscle precursor cells. These human muscle precursor cells are left to settle in a collagen coated dish, and then expanded in growth medium for at least one passage, preferably at least two passages, more preferably for a total of 3 or 4 passages.

A preferred cell culture medium, i.e. growth medium is free of fetal bovine serum (FBS).

According to a preferred embodiment of the invention, the growth medium is composed as described below.

Preferably, the hMPCs are expanded using a growth medium comprising hPL, preferably phPL, which preferably has been filtrated. A preferred type of phPL is BG O (platelets)/AB (plasma). Preferably, the final concentration of phPL in the growth medium is 5-20%, more preferably 7-12%, most preferably about 10% (volume percent).

An especially advantageous growth medium used for expansion of the human muscle precursor cells additionally comprises an anti-coagulation factor, preferably heparin. For this purpose, e.g. Heparin-Na (heparin-sodium) (25'000 IU/5 ml) can be used. The heparin is preferably added to the filtrated phPL thus forming a mixture, before adding said mixture to the nutrient solution of the growth medium to a preferred final concentration of 1-10 IU per ml of growth medium, more preferably 2-6 IU/ml, most preferably about 2 IU/ml. As an alternative, other substances preventing clotting (e.g. EDTA) can be used. In case of the use of fibrinogen-depleted phPL, no anti-coagulant must be added, as no active coagulation factors are present anymore.

The growth medium preferably additionally, besides the hPL or phPL, respectively, and the anti-coagulation factor, comprises the following ingredients:
  a nutrient solution, preferably Dulbecco's Modified Eagle Medium (DMEM), more preferably a 1:1 DMEM/F12 nutrient mix (1:1 mix of DMEM and Ham's F-12);
  human Epidermal Growth Factor (hEGF), preferably added to the nutrient solution to result in a final concentration of 2-20 ng/ml, more preferably about 10 ng/ml;
  human basic Fibroblast Growth Factor, (hbFGF), preferably added to the nutrient solution to result in a final concentration of 0.5-2 ng/ml, more preferably of about 1 ng/ml;
  insulin, preferably human insulin, preferably added to the nutrient solution to result in a final concentration of 5-20 µg/ml, more preferably of about 10 µg/ml;
  dexamethasone, preferably added to the nutrient solution to result in a final concentration of 0.2-0.8 µg/ml, more preferably of about 0.4 µg/ml.

The percentages indicated for the final concentration are calculated in volume percent of nutrient solution, however, for simplification purposes, a final/total volume of 500 ml of nutrient solution was used for the calculations (x vol per each 100 ml nutrient solution), and not the final cell culture-/growth medium composition (which slightly exceeds 550 ml due to the addition of the phPL). Furthermore, the dosis of heparin is not indicated in gram, but in international units (IU). One unit prevents the coagulation of 1 ml citrate-comprising-plasma after the addition of $CaCl_2$) at 37° C., over the time span of one hour.

The present invention further concerns a population of skeletal muscle derived human muscle precursor cells (hMPC) generated in a method according to the method described above. Preferably, the protein expression pattern of the population of skeletal muscle derived hMPC preferably is as follows: Pax7 (preferably at least 60%), Desmin (preferably at least 60%), MyHC (preferably about 30-50%), and alpha-actinin (preferably at least 50%, more preferably at least 60%). The cells preferably express less than 15% of CD34, serving as a negative control. As typically used in flow cytometry analysis, the percentages are "percent positive cells" which is a count-independent measure of the number of cells that are fluorescent, i.e. the indicated percentage of the total number of cells express the protein in question.

The inventive population of skeletal muscle derived hMPCs can be used as a medicament, especially for treating skeletal muscle dysfunction, such as e.g. stress urinary incontinence (SUI).

Furthermore, the invention provides an advantageous composition of a FBS-free cell culture medium or growth medium for the generation/production of said population of hMPCs for the treatment of skeletal muscle dysfunction. The inventive growth medium preferably comprises the composition described above.

According to a preferred embodiment, the cell growth medium, however, only for passage 0, further comprises a solution containing an antibiotic agent, preferably containing penicillin and streptomycin, preferably at a final concentration of about 1% (Pen/Strep: 10000 units/ml of penicillin and 10000 µg/ml of streptomycin in a 10 mM citrate buffer (for pH stability) at 20° C.).

The cell growth medium according to the invention, as mentioned above, preferably is prepared by carrying out the following steps:
  provision of a nutrient solution, preferably DMEM solution, more preferably a DMEM/F12 1:1 nutrient mix;
  addition of hEGF, preferably such that it reaches a final concentration of about 10 ng/ml in the nutrient solution;
  addition of hbFGF, preferably such that it reaches a final concentration of about 1 ng/ml;
  addition of insulin, preferably human insulin, preferably such that it reaches a final concentration of about 10 µg/ml;
  preparation of a mixture of filtrated human platelet lysate with an anti-coagulation factor, preferably heparin, more preferably Heparin-Na, preferably by adding heparin, preferably Heparin-Na to filtrated phPL before adding the mixture to the (DMEM) nutrient solution, preferably such that it reaches a final concentration of 5-20% of phPL, preferably a final concentration of 7-12% of phPL, more preferably a final concentration of about 10% of phPL, wherein preferably the heparin reaches a final concentration of 1-10 IU/ml, more preferably 2-6 IU/ml, most preferably 2 IU/ml of heparin, followed by addition of the mixture of phPL and heparin to the nutrient solution;
  addition of dexamethasone, preferably such that it reaches a final concentration of 0.2-0.8 µg/ml, more preferably about 0.4 µg/ml.

The present invention further provides a composition comprising a population of skeletal muscle derived hMPCs suspended in a collagen solution as a carrier matrix. Said composition is suitable for use in the treatment of skeletal muscle dysfunction.

The current invention further provides a method for the production of such a composition comprising a population of skeletal muscle derived hMPCs, wherein the population of hMPCs is preferably prepared according to the method described above. For the production of a composition which can be used in the treatment of skeletal muscle dysfunction, the population of human muscle precursor cells is suspended in a preferably low-percentage collagen solution, preferably of a 0.5-4 mg/ml, more preferably 1-2 mg/ml, preferably at a concentration of 10-40 million cells/ml of collagen solution, preferably 20-30 million cells/ml of collagen solution. Advantageously, the collagen solution preferably contains type I collagen, preferably of porcine, bovine or human origin.

The targeted cell count for injection into each patient is preferably in the range of 60-100 million cells total. Before injection, quality and purity analyses are performed.

To deliver a preferred minimum of 80 million hMPCs with at least 80% viability, in a final concentration of 20 million cells/ml, the cultured cells (80 million) are suspended in 4 ml of a collagen solution. The final product is preferably transported in a 10 ml syringe in a box at 5° C. (+/−3° C.) controlled by a temperature measuring device. In the surgery room, the final product is preferably mixed gently prior to injection.

By injecting the composition described above into a patient, preferably a human patient, preferably a female patient, more preferably into the same female human patient from whom the muscle biopsy was taken, it is possible to regenerate skeletal muscle tissue in the patient. In other words, the population of hMPC according to the present invention can be used in the manufacture of a medicament for treating skeletal muscle dysfunction in a human patient.

A further object of the invention is a method of treating skeletal muscle dysfunction, especially a defect of the external urethral sphincter muscle, and/or of regenerating skeletal muscle tissue in a human patient, using the composition according to the invention as described above. Said method of treatment comprises at least the following steps:

providing a composition comprising a population of skeletal muscle derived human muscle precursor cells suspended in a collagen solution, wherein the composition preferably is prepared according to the method described above;

injecting the composition into the urinary sphincter muscle of a human patient, preferably a human female patient, preferably under ultrasound guidance;

wherein after the injection of the composition, the pelvic floor of the human patient preferably is subjected to neuro-muscular electromagnetic stimulation (NMES).

Therefore, the above mentioned method of treatment can be used to treat stress urinary incontinence, which among others, can be caused by a defect of the external urethral sphincter muscle.

To allow standardized injections into the pelvic floor of human patients, preferably female human patients, the cells are injected under ultrasound guidance. Preferably 8-12 aliquots are injected into the pelvic floor, wherein preferably a total amount of 4 ml is not exceeded.

NMES-treatment following the injection of the cell suspension supports muscle and nerve regeneration by activating muscle-nerve cross-talk and induces the maturation of neuromuscular junctions. This non-invasive treatment, which can be applied to the pelvic floor by a chair containing a large electromagnetic coil in its seat (such as the specialized magnetic chair "BioCon-2000"), can support a sustained formation of functional muscle tissue.

Pelvic floor electromagnetic stimulation induces controlled muscle regeneration, depolarization of adjacent nerves and contraction of muscles. The physiologic stimulus of the pulsed magnetic field depends on some special design features that allow for a highly focused field and a very steep gradient of change at the advancing edge of the field. These characteristics produce a rapidly pulsing magnetic field that is readily adjustable in frequency and strength. For clinical effects, there is no advantage in removing the patient's external clothing. The strength of the induced electric field at maximum output is 120 V/m at the surface of the stimulation coil and this decreases exponentially with distance from the stimulation coil. At 5 cm above the stimulation coil, the field measures 22 V/m.

As the magnetic field pulses, the flux induces small eddy currents to flow in the tissues by generating the magnetic field containing the pulse. These currents will induce depolarization of nerve axons, and there will be a propagating nerve impulse that will travel both in a proximal and distal direction. If it is a terminal motor nerve axon, the propagating impulse will travel to the motor end plates and cause the obligatory release of acetylcholine, and there will be depolarization of the corresponding muscle fibers and contraction of those fibers. As the magnetic flux is regulated, the rate of contraction of the muscle fibers can be modulated within the usual physiologic ranges. It is possible to drive the rate of muscle fiber contraction to the maximum physiologic rate, on the order of 50 Hz The clinical efficacy of this extracorporeal magnetic treatment is to change the activity of pelvic muscles, and if the terminal motor nerve fiber is repeatedly activated, the motor end plate tends to be reinforced in terms of force and endurance.

Electromagnetic stimulation improves muscle regeneration by significantly minimizing the presence of inflammatory infiltrate and formation of scars after trauma. It avoids post-trauma muscle atrophy, induces muscle hypertrophy and increases the metabolism and turnover of muscle, tripling the expression of muscle markers and significantly improves the recovery of muscle function after trauma.

The proposed treatment of SUI is a therapeutic strategy based on implantation of autologous hMPCs in combination with NMES. In a future envisioned optimized method, the use of a bioreactor for the production of a population of hMPCs as a component of a cell-based medicinal product for the treatment of SUI would lower the production costs and thereby make the therapy accessible to a broader range of affected individuals.

Further developments include an optimization of the inventive process by use of a human collagen formulation produced according to a GMP-compliant method to omit the animal-components. In addition, the delivery of the inventive composition in the sphincter muscle is to be optimized in terms of precision in the future.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 10 shows a characterization of fiber formation in the tissue engineered skeletal muscle after subcutaneous injection of hMPCs in nude mice by H&E staining;

FIG. 11 shows the tracking of transplanted hMPCs by MRI;

FIG. 12 shows the signal decay curves for the tracking of transplanted hMPCs by T2*MRI (MRI-images not depicted);

DESCRIPTION OF PREFERRED EMBODIMENTS

Figure 15:
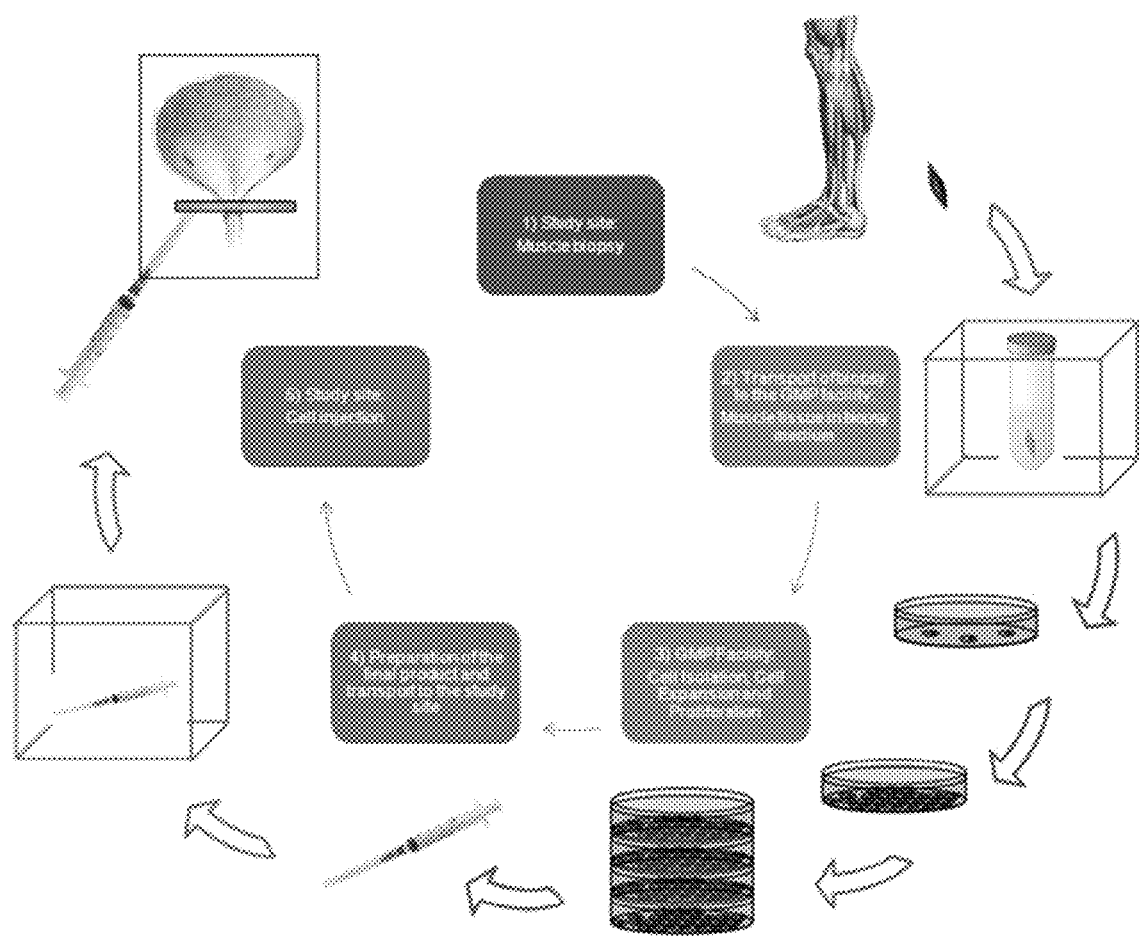
FIG. 15 shows the sequence of steps from biopsy over cell culture to treatment.

In FIG. 15, a summary is shown of the steps contributing to the present invention. First, a skeletal muscle biopsy is taken from the patient to be treated for skeletal muscle dysfunction. Next, the biopsy is processed and autologous hMPCs are isolated and expanded in cell culture, using an inventive cell growth medium. Following harvesting, the hMPCs are used for the preparation of a composition for use as a medicament, which is then injected into the patient, followed by NMES (not pictured).

Example 1

For the purpose of identifying an alternative to fetal bovine serum (FBS) that grants the proliferation of hMPCs and the efficient formation of contracting tissue engineered muscles, FBS in culture/growth medium of hMPCs was replaced by either human serum (HS) or pooled human platelet lysate (phPL).

Human biopsies from the rectus abdominis muscle were collected during abdominal surgeries. All samples were processed according to established protocols or by applying variations to this method (Eberli et al., Optimization of human skeletal muscle precursor cell culture and myofiber formation in vitro, Methods 47, 98, 2009). Briefly, each sample was minced and digested for 1 hour (37° C., 5% $CO_2$) in DMEM/F12 (Gibco, Invitrogen) enriched with 0.2% collagenase type I (Worthington Biochemical) and 0.4% dispase (Gibco). The digestion was stopped with growth medium supplemented with either FBS (FBS-GM), HS (HS-GM) or phPL (phPL-GM).

After centrifugation, the samples were resuspended in the respective growth medium and plated on collagen-coated 6 well dishes. In order to reduce the number of fast adhering fibroblasts, the suspension containing hMPCs was re-plated after 24 hours on new collagen-coated 6 well dishes. hMPCs were expanded at 37° C. in 5% $CO_2$ with growth medium supplemented either with FBS, with HS or with phPL. For experimental purposes, concentrations of phPL of 5%, 10% and 20% were tested.

The following composition of the growth medium was used: DMEM/F12 (Gibco, Invitrogen) supplemented with either 18% FBS (Gibco, Invitrogen), 10% HS (Invitrogen), or May 10, 2020% phPL (following the protocol in Schallmoser et al., 2007, obtained from Universitätsinstitut für Transfusionsmedizin, Salzburger Landeskliniken und Paracelsus Medizinische Privatuniversität, Salzburg, Austria). Additional supplements were similar for all growth medium variations: 1% penicillin/streptomycin (Gibco, Invitrogen) (for passage 0 only), 10 µg/ml human epidermal growth factor (hEGF) (Sigma), 1 µg/ml human basic fibroblast growth factor (hbFGF) (Sigma), 10 µg/ml human insulin (Sigma) and 0.4 µg/ml dexamethasone (0.5 µM, Sigma).

All experiments were done in triplicates for each sample from passage 1 to 3.

Following the expansion phase, the cells were transplanted subcutaneously into nude mice and after 4 weeks the formed tissue was harvested. hMPCs were characterized at different time points applying several criteria for identity, purity, and function. In vitro analysis was done by growth analysis, flow cytometry analysis, immunofluorescence staining and fiber formation assay. In vivo tests were done by immunohistochemistry, Western blot and myography. For the in vitro tests, the experiments were performed with at least 4 biopsies of patients in triplicate.

HS was chosen as an alternative to FBS for culturing hMPCs because of its successful application with other cell types such as chondrocytes, mesenchymal stem cells, corneal epithelial cells, and dental pulp stem cells. However, the growth medium supplemented with HS was not capable of sustaining the proliferation of hMPCs, the cells did not adhere to the culture dishes, even after 2 weeks and in cell cultures of biopsies originating from 4 different patients (data not shown). Even higher concentrations of 20% or higher of HS did not yield promising results despite speculations.

Figure 1:
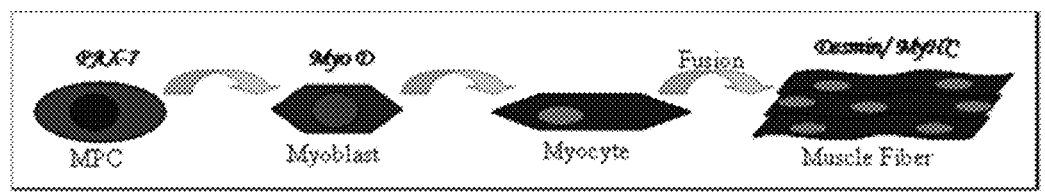
FIG. 1 shows, in a schematic way, the differentiation of hMPC in culture.
Figure 2:
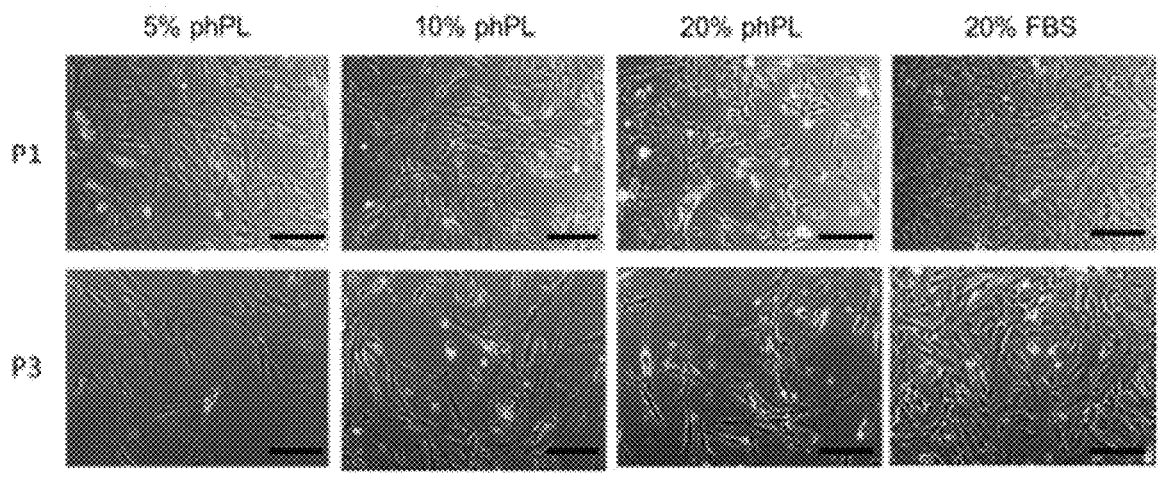
FIG. 2 shows a comparison of morphology of cultured hMPC in different growth media.

Morphological structures of growing cells were similar among the cells grown in FBS-supplemented growth medium (FBS-GM) and cells grown in phPL-supplemented growth medium (phPL-GM) at early and late passages (1 and 3), though less confluent for the xeno-free medium (FIG. 2). No differences were observed among the different concentrations of phPL in all passages.

Figure 3:
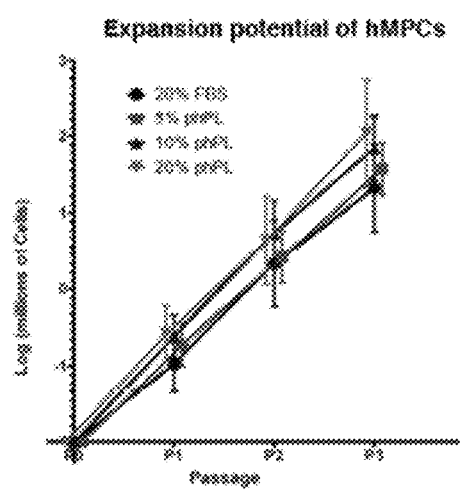
FIG. 3 shows a comparison of growth potential of cultured hMPCs in different growth media.

For the analysis of the growth potential of the hMPC cultured in different growth media, following the primary culture after biopsy, hMPCs were seeded at 5000 cells/cm² at each passage, cultured until 90-95% confluency and counted. The proliferation of hMPCs in either FBS-GM or phPL-GM was efficient and the same growth potential was observed during the first three passages (FIG. 3). However, the conditions with growth medium containing 10% and 20% phPL appeared to offer the best conditions for hMPCs to expand in vitro, resulting in more cells at the end of passage 3. Cells cultured in 10% phPL-GM were growing better in small dishes than in growth medium supplemented with 5% and 20% phPL-GM. Furthermore, after passage 3, the hMPCs cultured in 20% phPL-GM were growing and a proliferation arrest was witnessed. The 10% phPL-GM seemed to promote the proliferation of hMPC even more than the standard growth medium using FBS.

Obviously, media composition and -adjustment are cell-specific and critical for successful cell expansion and myogenic differentiation and explain why Kramer et al. (2005) were not able to optimally replace FBS by phPL. The missing supplements of growth factors such as hEGF, bFGF and insulin, and the use of a 20% concentration of phPL which is not the optimal concentration as discussed above, might be the reason. hMPCs were cultured until they were 80-90% confluent prior to flow cytometry analysis.

The effect of phPL on the myogenic profile of hMPCs was studied by immunofluorescence and flow cytometry analysis. phPL maintains the myogenic cell markers and phenotypes of hMPCs and differentiation potential that is well expressed in vivo.

Figure 4:
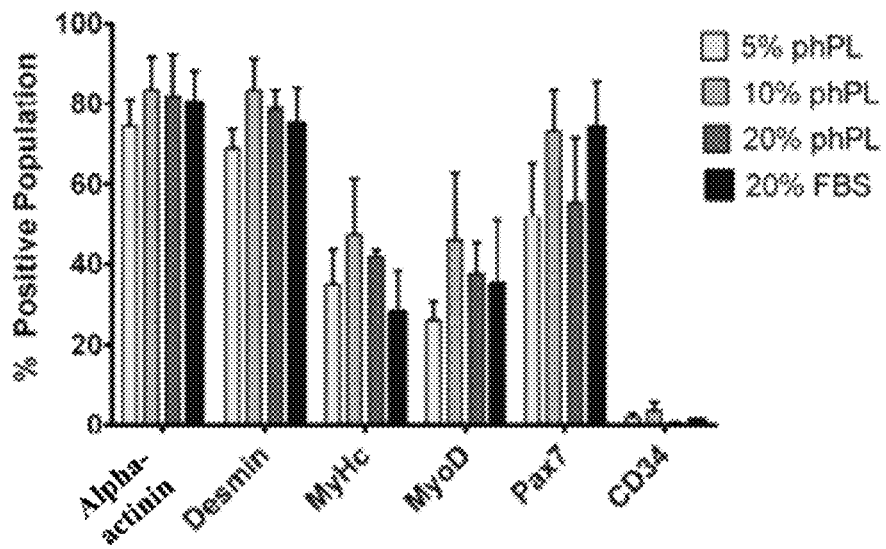
FIG. 4 shows a comparison of flow cytometry analysis of cultured hMPCs in different growth media.

The flow cytometry analysis of hMPCs cultured in different conditions (FBS or phPL) showed the expression of muscle specific markers at passage 3 (n=4 biopsies). The 10% phPL culture condition seems to promote the proliferation of hMPC even more than the standard condition (FBS-GM). However, the differences among the xeno-free conditions, as well as between phPL-GM and FBS-GM were not significant. In the growing cell populations, myogenic differentiation markers Alpha-actinin, Desmin, MyHC (myosin heavy chain), MyoD and Pax7 were expressed at about 80% for alpha-actinin, about 78% for Desmin, about 40% for MyHC, about 35% for MyoD, and about 65% for Pax 7, respectively (FIG. 4). The 10% phPL condition was chosen for further studies and comparison with FBS-GM condition.

Figure 5A:
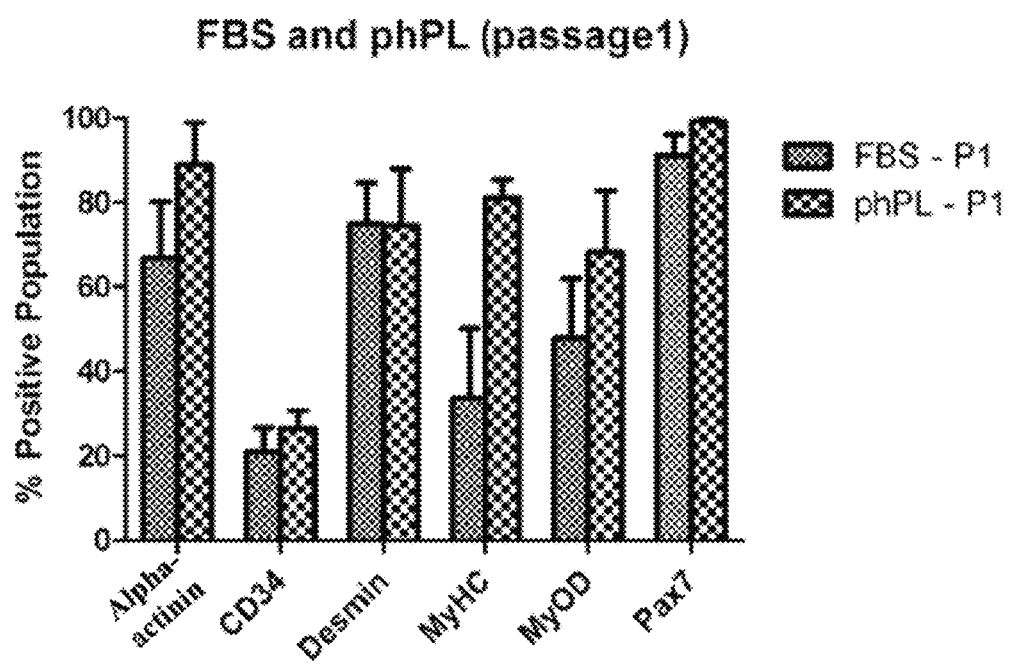
FIGS. 5a-5c show a comparison of hMPCs cultured in two different conditions for myogenic characterization, wherein in FIG. 5a, flow cytometry analysis is shown of hMPCs for passage 1, in FIG. 5b for passage 2, and in FIG. 5c for passage 3.
Figure 5B:
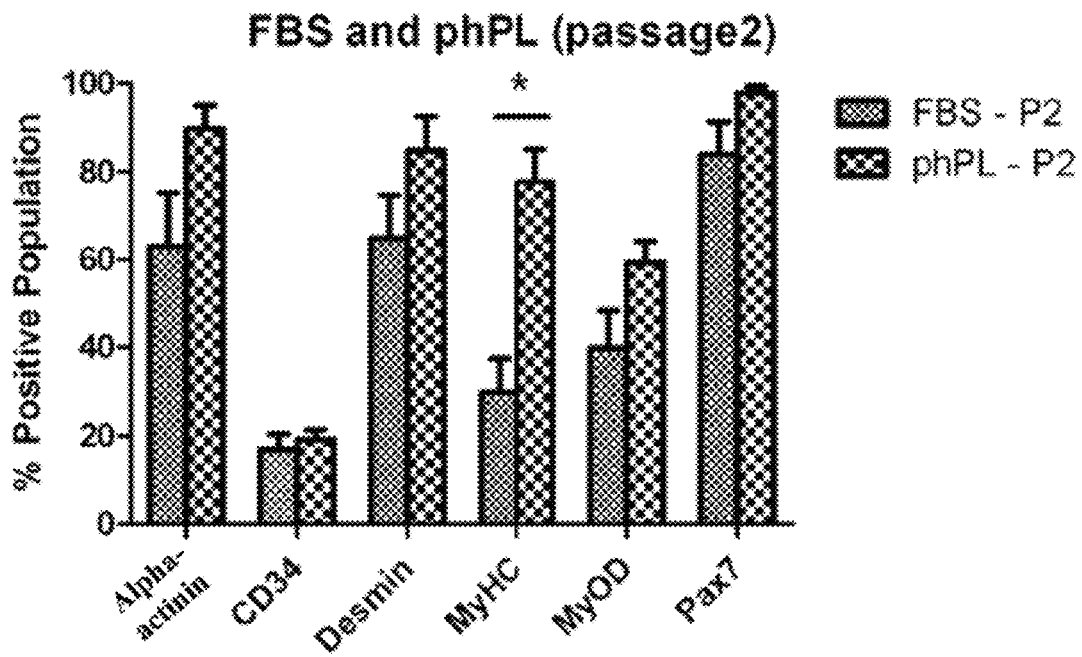
Figure 5C:
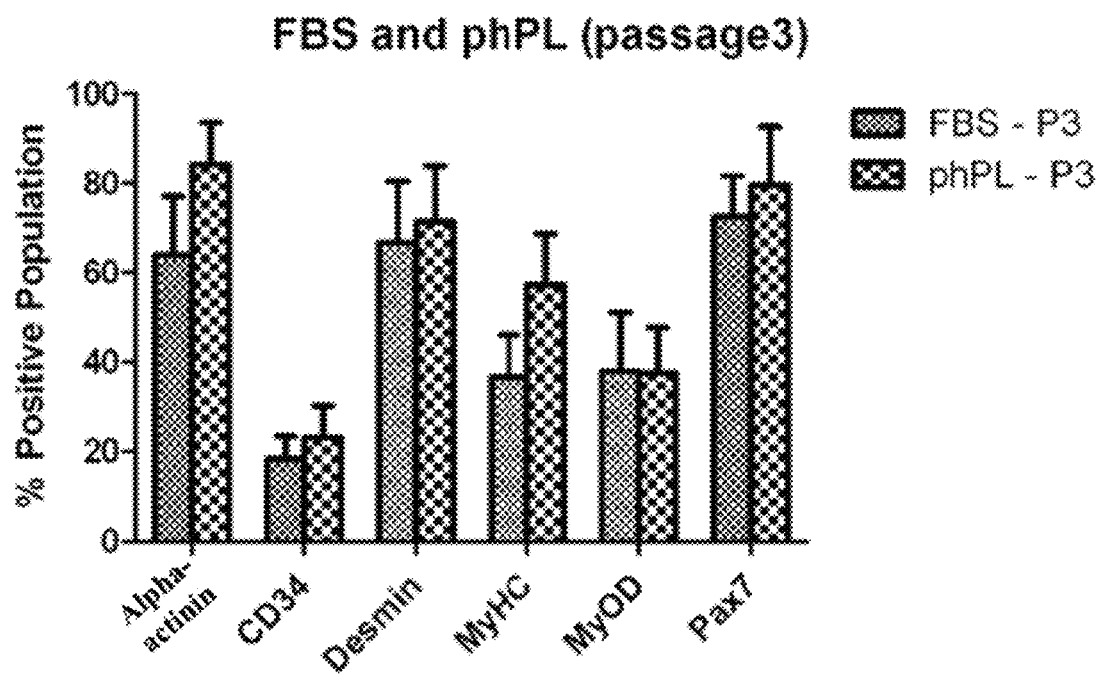
Figure 6:
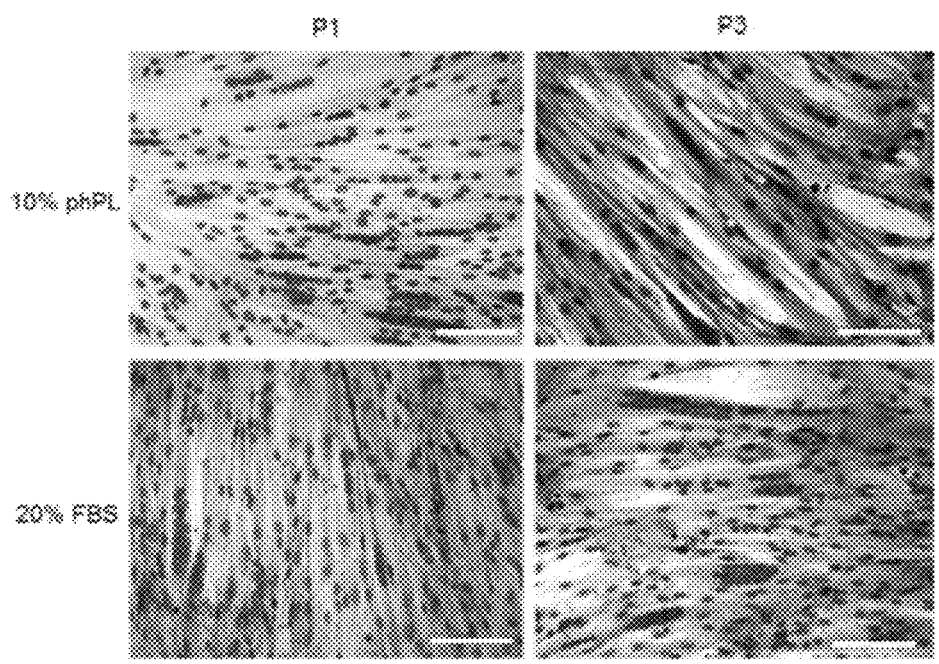
FIG. 6 shows a fiber formation assay for hMPCs cultured in differentiation medium containing either FBS or 10% phPL.

The expression of the skeletal muscle markers was comparable among FBS and phPL conditions over all passages, except for MyHC (FIGS. 5*a-c*). The latter was 2-fold higher in the phPL alternative in passage 1 and 2.5 times higher in passage 2, while there was no difference in passage 3. Both conditions represented ideal settings and favored the proliferation of hMPCs (rather than fibroblasts). CD34 detection stayed low and stable over all passages. Noteworthy is the slight decrease in the percentage of muscle markers expressed by MPCs from passage 1 to 3, in both FBS- and phPL-GM. This did not prevent the fusing of cells or the formation of myotubes in both environments (FIG. 6).

Figure 7:
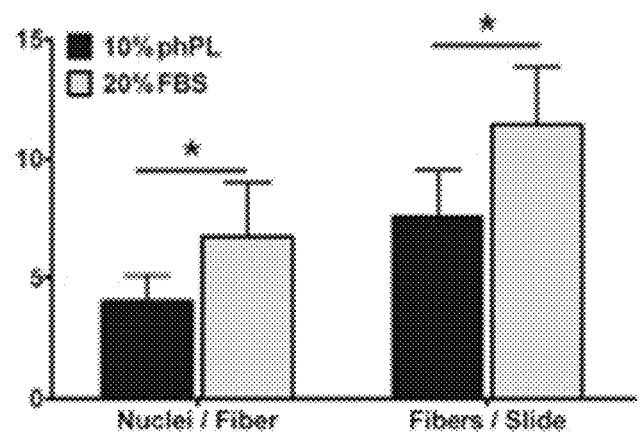
FIG. 7 shows a fiber formation analysis comparing hMPCs cultured in differentiation medium containing FBS with hMPCs cultured in differentiation medium containing 10% phPL.

Triggering the differentiation of skeletal cells, fiber formation of hMPCs could be observed by Giemsa staining. However, the fiber counting illustrated a different capacity of hMPCs grown in FBS-GM or phPL-GM in constructing muscle-like structures. It appears that hMPCs cultured for two weeks in FBS-GM fused and formed fibers more easily (11.4 fibers/slide (+2.4)) than hMPCs expanded in phPL (7.56 fibers/slide (+1.9)) (FIG. 7). The expression of skeletal muscle markers in both cell culture conditions was confirmed by immunocytofluorescence (not shown). Staining of the cultured hMPCs at passage 3 of hMPCs cultured with FBS-GM or 10% phPL-GM in vitro showed expression of the specific skeletal muscle markers Alpha-actinin, Desmin, MyHC and MyoD. The growth medium used for the fiber formation assays, i.e. differentiation medium, contained no growth factors (such as EGF, FGF, etc.).

Figures 8A, 8B:
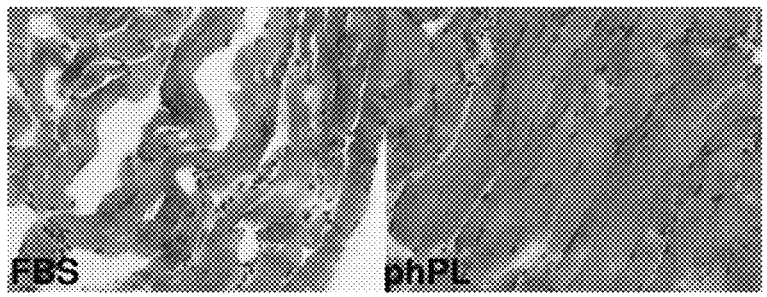
FIGS. 8a-8b show fiber formation in tissue-engineered muscle generated from subcutaneously injected hMPCs cultured with differentiation medium containing either FBS (FIG. 8a) or 10% phPL (FIG. 8b)

Following the in-vitro experiments, hMPCs cultured in FBS-GM and in 10% phPL-GM were injected subcutaneously into the back of nude mice. After four weeks, the animals were sacrificed and the engineered muscle tissues were extracted. The engineered tissues were visible in the transplantation area of all conditions. In addition, H&E staining demonstrated muscle-like structures in engineered muscle tissues (FIGS. 8*a, b*). The 40× magnification details and highlights the muscle formation with myotube structures.

Western blot performed on samples 4 weeks post-injection confirmed the expression of the muscle specific markers Alpha-actinin, Desmin, MyHC and MyoD in both culture conditions (not shown). Immunohistochemical analysis confirmed the muscular characterization of the in vivo samples. Transplanted hMPCs were labeled with PKH67 before injection. The engineered tissues of both conditions were detected with this label.

Figure 9:
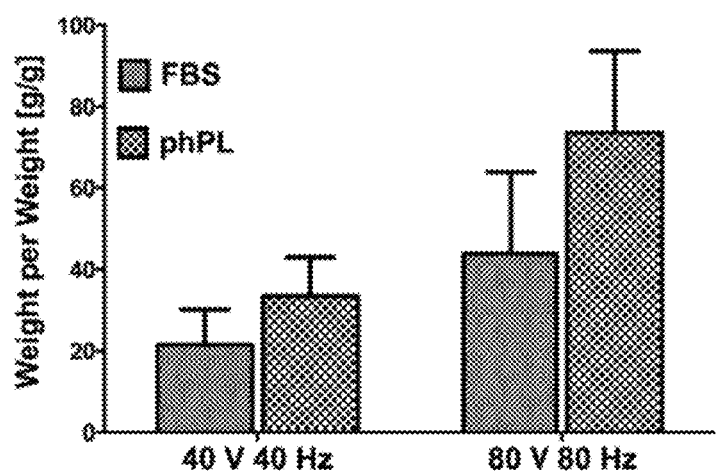
FIG. 9 shows an organ bath analysis performed at two levels of stimulation.

The muscle specific markers Alpha-actinin, Desmin, MyHC and Pax7 were expressed in the engineered tissues originating of both, hMPCs cultured in FBS-GM and 10% phPL-GM (not shown). Finally, these tissue-engineered harvests were contracting when stimulated at 40V/40 Hz and 80V/80 Hz (FIG. 9). Although the phPL-GM condition seemed to provide a better contractility compared to the standard condition, the observed difference was not statistically significant.

To summarize, hMPCs were able to proliferate in FBS-based growth medium and growth medium supplemented with all tested concentrations of phPL (5-20%). phPL has shown to sustain the expansion of hMPCs capable of fusing and forming contracting tissue-engineered muscle in vivo in a manner similar to FBS. Therefore, phPL can be used as a substrate for FBS in cell culture, preserving the characteristics of hMPCs to proliferate and the expression of myogenic cell surface markers. Although subtle differences between FBS and phPL expanded hMPCs have been identified, the differentiation potential of the cells to form myotubes in vivo remains constant. This finding can promote the clinical application of a cell-therapy with hMPCs isolated from muscle biopsies to treat patients suffering from SUI.

Example 2

Biopsy:

Provided that the patient did not meet any of the exclusion criteria and met all inclusion criteria, the biopsy was taken under general or spinal anesthesia. The biopsy was taken from the musculus soleus (a skeletal muscle which is very similar in composition to the sphincter muscle) of the left or right leg. For this purpose, an incision (approx. 2-4 cm) a few centimeters below the popliteal fossa on the back side of the lower limb was performed. The musculus soleus was then identified and a piece of the muscle (about 1 cm$^3$) was surgically removed. The sterile muscle biopsy was transferred immediately after harvesting to a closed 50 ml tube containing transport medium (PBS with 1% Penicillin/Streptomycin) and processed within 24 hours, preferably within 6 hours, more preferably immediately after biopsy in a GMP laboratory. The fascia, subcutaneous tissue and skin were sutured in routine fashion. Wound control and removal of the skin sutures were performed one week after biopsy.

Preparation of a hMPC-Population and Cell-Culture:

In the laboratory, fat- and tendon tissue were surgically removed under laminar flow, followed by rinsing in PBS and disinfection in a 1:1 solution containing a disinfectant and PBS. The remaining tissue was cut into small tissue pieces of about 1×1 mm using scissors and a forceps, then placed into 5 ml of a solution of 0.2% collagenase and 0.4% dispase and incubated for at least 1 hour at 37° C. for enzymatic digestion. After incubation the tissue pieces were aspirated with a 25 ml pipette and placed in a 50 ml tube, where they were washed with growth medium as listed below to block the enzymatic reaction.

Subsequently, the sample was centrifuged for 5 minutes at 1500 rpm, after which the supernatant was removed. 15 ml of growth medium composed according to the recipe listed below were added to the cell pellet and the mixture was homogenized by pipetting up and down at least 10 times. Then, a cell strainer with a pore size of 100 µm was placed on the tube and the sample was filtered.

Meanwhile, a 6-well dish was pre-coated with a collagen solution. After 1 h, the collagen solution was aspirated and the wells were washed 3 times with PBS to remove the acidic environment.

After removing the PBS from the collagen-coated wells, the cells suspended in growth medium were split into the first two wells of a collagen-coated 6-well dish. Two other wells were filled with PBS, which is removed prior to adding cells in a subsequent step.

The presence of single fibers was confirmed by phase microscopy and all dishes were incubated over night at 37° C. and humidified atmosphere containing 5% $CO_2$.

In order to increase the purity of the hMPCs, the cells were submitted to a fibroblast reduction step: As fibroblasts tend to adhere to the plate first, the supernatant containing non adhered hMPCs was transferred after 20-28 hours to the next collagen type I coated well on the same plate after removing the PBS. The growth medium was changed at day 4 and 7. If the hMPCs were not yet adherent, medium was not changed on day 4. Instead, some fresh growth medium war carefully added on top. For the medium change, around 80% of the old medium was carefully removed and fresh medium was slowly added. The primary cultured cells reached 80% confluency within 8-10 days post-plating in the 6-well plate. Splitting was done respecting the final concentration of 3000-7000 cells/$cm^2$, optimally about 5000 cells/$cm^2$. After the transfer from the 6-well plate to large culture plates, a growth medium was used which was not supplemented with antibiotics any more.

Cell morphology, cell numbers and fiber formation were evaluated at every passage.

The following protocol was used for the production of the hMPC-growth medium for the expansion of hMPCs:

The following materials were used:
- a 500 ml bottle of DMEM/F12 nutrient mix (1:1, Gibco) stored at 4° C.;
- 500 µl of hbFGF (Sigma, 500 ng in 500 µl at −80° C.) (final concentration of 1 ng/ml);
- −1 ml of hEGF (5 µg/ml at −80° C.) (final concentration of 10 ng/ml);
- 500 µl of human insulin (Sigma, 5 mg in 500 µl at −20° C.) (final concentration of 10 µg/ml);
- 1.2 ml of dexamethasone (Sigma, 200 µg in 1.2 ml at −20° C.) (final concentration of 0.4 µg/ml);
- −50 ml filtrated human platelet lysate (hPL) (BG 0 (platelets)/AB (plasma)) (final concentration of 10%);
- 600 µl Heparin-Na (Braun, 3511014) (25'000 IU/5 ml), added to the filtrated hPL before adding to the DMEM (final concentration of Heparin-Na of 6 IU per ml of growth medium);
- Pen/Strep (6 ml of 10'000 units/ml of penicillin and 10'000 µg/ml of streptomycin at −20° C.) only for medium used for passage 0 (final concentration of 1%).

Thereby, a culture technique was established that uses only collagen-coated dishes and defined media for expansion and differentiation of hMPCs. Cell characterization demonstrated that the hMPC phenotype can be maintained under these conditions and that the cells have the ability to form myofibers in vitro and in vivo. Sufficient numbers of cells for tissue engineering applications can be grown in 3-4 weeks using this method.

Preparation of Cell Composition:

Before injection, a sample of the cells is analyzed by flow cytometry, and viability tests are performed to investigate quality and purity. To deliver a minimum of 80 million mMPCs with at least 80% viability, i.e. about 64 million viable cells, in a final concentration of 20 million cells/ml, the cultured cells (about 80 million) are suspended in 4 ml of a low percentage collagen solution, i.e. 3-4 mg/ml, leading to a final concentration of about 2 mg/ml collagen in the final product. For the carrier matrix, only a low concentration of collagen is necessary. This compares to previous studies using higher collagen concentrations, which only lead to good short-term results.

As for the preparation of the collagen solution, the collagen was mixed in 0.01 M HCl. Then MEM was added as a pH indicator, until the solution turned yellow. Then $NaHCO_3$ was added dropwise until the solution turned pink, i.e. reaches a physiological pH-value of pH 6-8. The collagen solution was then transferred unto the final cell pellet (harvested after passage 2), homogenized by pipetting up and down, transferred into a 50 ml tube and cooled in a cooler device.

The optimal maximal shelf-life of the finalized composition of hMPCs in a collagen solution is limited. The stability of the final composition is up to 24 hours at 2-8° C.

Therefore, the finalized composition should be administered as fast as possible, preferably within 4 hours, at the latest within 24 hours after preparation, to maintain at least 80% cell viability.

The final product in the 10 ml syringe is transported in a box at 5° C. (+/−3° C.) controlled by temperature measuring device to the study site. In the surgery room, the final product is mixed gently before injection.

Injection of hMPC-Composition:

The treatment of SUI with hMPCs is restricted to a damaged sphincter muscle of low-risk adult female patients (according to specific exclusion criteria) with a history of SUI.

To allow standardized injections into the pelvic floor of female patients, the cells are injected under ultrasound guidance.

An ultrasound probe is positioned transvaginally and a guidance tool comprising a tube and one-way syringes, is placed into the urethra. 8-12 aliquots of the hMPC-collagen composition are injected into the pelvic floor, not exceeding a total amount of 4 ml of the composition.

A sample of cells to be injected may be cultured for fiber formation assay and flow cytometry assays to check their capability in forming fibers and in expressing myogenic markers.

For comparative purposes, different injection options (transurethral and transvaginal) were evaluated, as well as transvaginal ultrasound (BK 8848, BK Medical, Denmark)-guided injections of fluid polymer compounds (liquid polymer which hardens after application) into urinary sphincter muscles of Thiel fixated human cadavers. The sphincter was then analyzed by MRI and histology of whole mount sections. Both methods showed good and comparable accuracy in hitting the rhabdosphincter.

However, the transurethral approach seems to be superior in means of simplicity primarily due to handling and shorter learning curve.

Electromagnetic Stimulation:

Physiotherapy for pelvic floor exercises was performed by electromagnetic chair stimulation (BioCon-2000). The strength of the induced electric field at maximum output was 120 V/m at the surface of the stimulation coil. At 5 cm above the stimulation coil, the field measured 22 V/m.

Figure 13A:
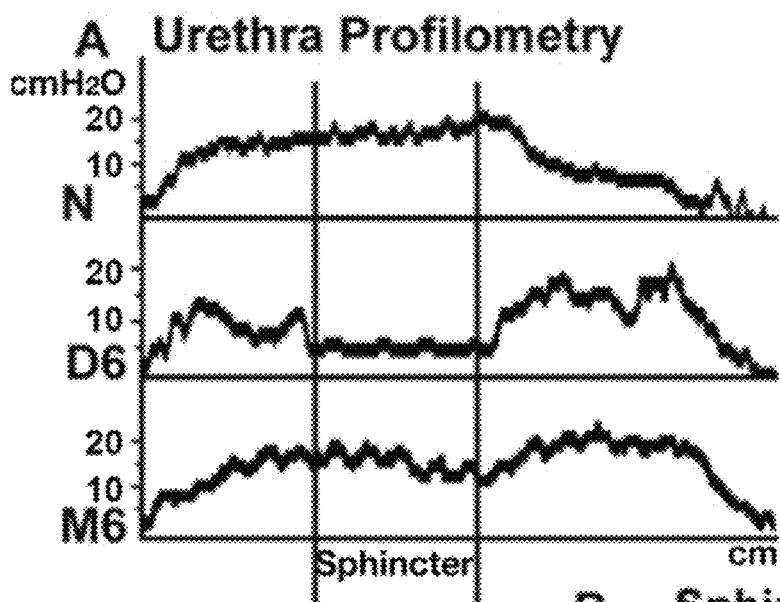
FIGS. 13a-13b show a functional assessment of sphincter function in a canine model, wherein in A, representative urethra profiles are shown, and in B, a graph showing sphincter pressures over time are shown.
Figure 13B:
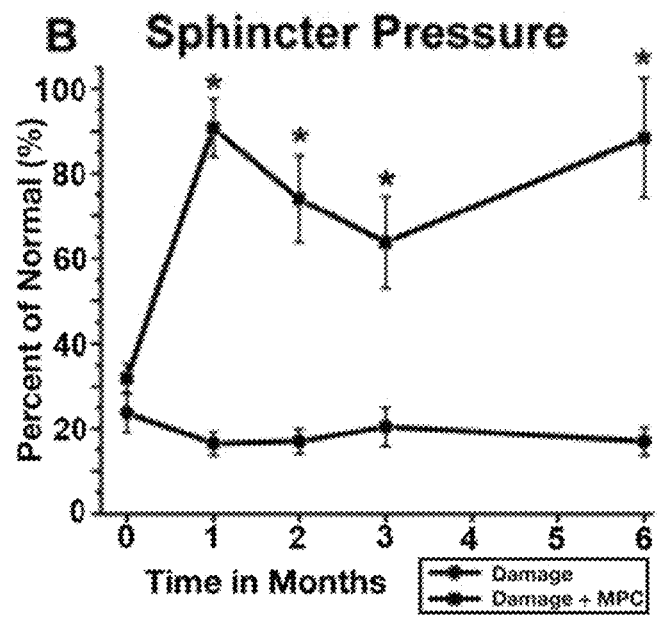
Figure 14:
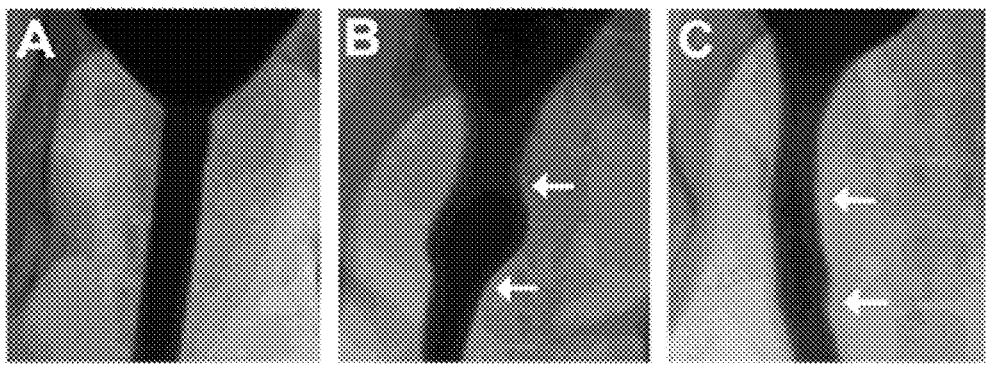
FIG. 14 shows a radiogram of the dog sphincter area at 6 months, wherein in A, the image for a normal animal sphincter, in B for a damaged sphincter, and in C for a damaged sphincter treated with MPC is shown.

Analysis of Muscular Differentiation and Function in Animal Models:

For studying the effect of MPCs on skeletal muscle regeneration, several animal models were used: mouse (subcutaneous cell injection for ectopic muscle formation (FIG. 10) and crush injury models of quadriceps and tibialis hindlimb muscles (not shown)); rat (bladder outlet obstruction model); dog (urethral sphincter insufficiency model by microsurgical incision of the external sphincter) (FIGS. 13 and 14).

For the characterization of fiber formation in the tissue engineered skeletal muscle after injection of hMPCs in nude mice, cultured primary hMPCs were injected subcutaneously in nude mice. 3, 7, 14 and 28 days after injection, the formed tissue was harvested and analyzed by H&E staining. Increasing fiber formation capacity by the injected hMPCs was observed within four weeks with histologically mature muscle tissue at day 14, as shown in FIG. 10. Immunohistofluorescence staining confirmed the expression of skeletal muscle markers Alpha-actinin, MyHC, and Desmin (not shown).

As an example for non-invasive visualization of the cells' differentiation by MRI, hMPCs were tracked by MRI and the developing muscle tissue by T2*MRI (FIGS. 11 and 12).

FIG. 11 shows the tracking of transplanted MPCs by MRI. Unlabelled (control) and MPCs labelled with 400 µg/ml superparamagnetic iron oxide (SPIO) were injected subcutaneously on the back of nude mice. Mice were scanned by MRI 4 days, and 1, 2, and 4 weeks after injection. T2-weighted MRI images of the area of interest are shown.

Injected cells are marked with an arrow. In FIG. 12, the T2* signal decay curves for all measurement time points are shown. The maturation of muscle precursor cells into skeletal muscle fibers was observed, correlating with a decrease in relaxation and diffusion parameters (measured by MRI). Importantly, during differentiation, the relaxation and diffusion parameters decreased, approaching the values for mature skeletal muscle tissue, suggesting that MRI relaxation and diffusion measurements provide adequate biomarkers for the in-vivo monitoring of muscular differentiation and function.

FIG. 13 shows a functional assessment of sphincter function in a canine model. Canine muscle progenitor cells were successfully and reproducibly isolated, grown and expanded.

In A, representative urethra profiles show the increase of sphincter pressure in the sphincter area after cell treatment. N shows the normal control, D6 shows the "damage only" control at 6 months, and M6 shows the MPC treated animal at 6 months. In B, the graph shows sphincter pressures over time. The animals injected with cells showed a significant functional recovery of their sphincter function with sphincter pressures approximately 80% of normal, while the pressures in the control animals ("damage only") dropped and remained at 20% (p<0.025). Histologically, the implanted cells survived and formed tissue within the injected region of the sphincter and formed new innervated muscle fibers (see also Eberli, D., et al., Muscle Precursor Cells for the Restoration of Irreversibly Damaged Sphincter Function. Cell Transplant, 2012).

In FIG. 14, a radiogram of the dog sphincter area at 6 months is shown. Animals treated with MPC injection were able to regain a normal anatomical sphincter structure (arrows in C) and bladder neck region while animals without treatment showed a widening of the sphincter area (arrows in B), indicating a loss of anatomic integrity. A shows a representation of a normal, undamaged sphincter, B of a damaged sphincter, and C of a damaged sphincter treated with MPC.

The results in dogs showed that autologous MPCs are able to restore otherwise irreversibly damaged sphincter function. The injected cells were able to survive and formed mature tissue within the damaged sphincter function. This large animal study demonstrated the feasibility of using autologous muscle precursor cells for functional restoration of urinary sphincter muscle in patients with sphincter insufficiency.

For successful application of MPCs in muscle cell therapy in humans, a non-invasive in-vivo monitoring tool of the differentiation process is crucial. MRI relaxation and diffusion measurements provide adequate biomarkers for the in-vivo monitoring of muscular precursor differentiation.

The invention claimed is:

1. A method for treating a skeletal muscle dysfunction, which is stress urinary incontinence in a female human patient, the method comprising the steps of:
providing a composition comprising a population of skeletal muscle derived human muscle precursor cells suspended in a collagen solution,
wherein the composition is prepared according to the following steps:
surgically removing at least one of the tissues selected from the group consisting of fat, tendon, and connective tissue from a human tissue sample from a skeletal muscle biopsy of a human patient;
mincing and enzymatic digestion of the human tissue sample;
reducing a number of fibroblast cells, thereby yielding a population of skeletal muscle derived human muscle precursor cells;
allowing the human muscle precursor cells to settle in a collagen coated dish;
expansion of the skeletal muscle derived human muscle precursor cells in a cell growth medium for at least one passage, wherein the cell growth medium is free of fetal bovine serum and comprises 10% human platelet lysate; and
suspending of the skeletal muscle derived human muscle precursor cells in a collagen solution at a concentration of 10-40 million cells/mL with at least 80% viability, thereby yielding a composition comprising the population of skeletal muscle derived human muscle precursor cells suspended in a collagen solution, wherein the concentration of collagen in the composition is 2 mg/ml; and
injecting the composition into a skeletal muscle of the female human patient in need thereof, wherein the injection is performed via transurethral injection.

2. The method according to claim 1, wherein the composition is injected into a skeletal muscle of the same human patient whose human tissue sample was used for preparing the composition.

3. The method according to claim 1, wherein the collagen solution contains type I collagen of porcine, bovine or human origin.

4. The method according to claim 1, wherein after the injection of the composition, the human patient is subjected to neuro-muscular electromagnetic stimulation (NMES).

5. The method according to claim 1, wherein the skeletal muscle biopsy is taken from a tissue selected from the group consisting of musculus soleus, rectus abdominis, quadriceps femoris, and vastus lateralis.

6. The method according to claim 1, wherein the skeletal muscle derived human muscle precursor cells are cultured for at least 2 passages.

7. The method according to claim 1, wherein the cell growth medium further comprises an anti-coagulation factor, and wherein the cell growth medium additionally comprises at least one of the following ingredients:
   a nutrient solution;
   hEGF;
   hbFGF;
   insulin; and
   dexamethasone.

8. The method according to claim 7, wherein for at least one passage, the cell growth medium further comprises a solution containing an antibiotic agent.

9. The method according to claim 7, wherein the nutrient solution is Dulbecco's Modified Eagle Medium (DMEM).

10. A combination therapy in a female human patient for the treatment of stress urinary incontinence in the female human patient in need thereof,
    comprising transurethral injection of a composition comprising a population of skeletal muscle derived human muscle precursor cells suspended in a collagen solution at a concentration of 10-40 million cells/mL with at least 80% viability into the human patient, wherein the concentration of collagen in the composition is 2 mg/ml, followed by neuro-muscular electromagnetic stimulation (NMES) of the human patient, wherein the population of skeletal muscle derived human muscle precursor cells is generated according to the following steps:
      surgically removing at least one of the tissues selected from the group consisting of fat, tendon, and connective tissue from a human tissue sample from a skeletal muscle biopsy of a human patient;
      mincing and enzymatic digestion of the human tissue sample;
      reducing a number of fibroblast cells, thereby yielding a population of skeletal muscle derived human muscle precursor cells;
      allowing the human muscle precursor cells to settle in a collagen coated dish;
      expansion of the skeletal muscle derived human muscle precursor cells in a cell growth medium for at least one passage, wherein the cell growth medium is free of fetal bovine serum and comprises 10% human platelet lysate.

11. The combination therapy according to claim 10, wherein the population of skeletal muscle derived human muscle precursor cells are autologous.

12. The method according to claim 10, wherein the skeletal muscle biopsy is taken from a tissue selected from the group consisting of: musculus soleus, rectus abdominis, quadriceps femoris, and vastus lateralis.

13. The method according to claim 10, wherein the skeletal muscle derived human muscle precursor cells are cultured for at least 2 passages.

14. The method according to claim 10, wherein the cell growth medium further comprises an anti-coagulation factor, and wherein the cell growth medium additionally comprises at least one of the following ingredients:
    a nutrient solution;
    hEGF;
    hbFGF;
    insulin; and
    dexamethasone.

15. The method according to claim 14, wherein for at least one passage, the cell growth medium further comprises a solution containing an antibiotic agent.

* * * * *